United States Patent [19]

Juvinall

[11] Patent Number: 4,487,322

[45] Date of Patent: Dec. 11, 1984

[54] METHOD FOR INSPECTING GLASS CONTAINERS

[75] Inventor: John W. Juvinall, Ottawa Lake, Mich.

[73] Assignee: Owens-Illinois, Inc., Toledo, Ohio

[21] Appl. No.: 424,687

[22] Filed: Sep. 27, 1982

[51] Int. Cl.³ .............................................. B07C 5/342
[52] U.S. Cl. .................................. 209/526; 209/588; 250/223 B; 356/240; 358/106
[58] Field of Search .............................. 209/522–524, 209/526, 528, 552, 576–577, 588; 358/101, 106, 107; 356/240, 434, 435, 394; 250/223 B; 350/314

[56] References Cited

U.S. PATENT DOCUMENTS

| 2,326,007 | 8/1943 | Capstaff | 350/314 |
| 3,886,356 | 5/1975 | Gomm et al. | 250/223 B |
| 3,926,525 | 12/1975 | Sheldrick | 350/314 X |
| 3,987,301 | 10/1976 | O'Conner | 250/223 B X |
| 4,376,951 | 3/1983 | Miyazawa | 250/223 B X |
| 4,378,495 | 3/1983 | Miller | 209/526 X |

Primary Examiner—David A. Scherbel
Assistant Examiner—Glenn Foster
Attorney, Agent, or Firm—Gerald T. Welch; Myron E. Click

[57] ABSTRACT

A method for detecting a substantially transverse refractive defect in the sidewall of a transparent container is disclosed. The method comprises the steps of directing a filtered source of diffused light toward the sidewall of the container to provide an intensity gradient varying in a direction substantially parallel with the longitudinal axis of the container and sensing the intensity of light at a plurality of positions in a field-of-view aligned along a path in the plane of the sidewall and generally parallel with the longitudinal axis of the container. The method further comprises the step of producing a plurality of pixel signals each having a magnitude corresponding to the intensity of light sensed at each position in the field-of-view, whereby the shape of the wave train of pixel signals corresponds to the longitudinal intensity gradient in the absence of a transverse refractive defect and a detectable defect signature superimposed on the longitudinal gradient in the presence of a transverse refractive defect. The method finally includes the steps of analyzing the wave train of pixel signals to detect the presence of a defect signature and rejecting the container in response to a defect signal.

6 Claims, 6 Drawing Figures

METHOD FOR INSPECTING GLASS CONTAINERS

FIELD OF THE INVENTION

The present invention relates in general to the inspection of glass containers and more particularly to a method for detecting transverse refractive defects in the sidewall of a glass container.

BACKGROUND OF THE INVENTION

Glass containers are typically formed by forcing gas into the interior of a parison of semimolten glass in a mold. The glass parison expands against the interior surfaces of the mold to form a bottom, and a sidewall with an annular rim defining an opening of the container. During the forming process, various types of defects may be formed, some of which require the container to be rejected. At first, containers were manually inspected by the human eye, but this method proved to be costly, time consuming and inaccurate. Thus, automatic inspection devices were employed in order to reduce the inspection cost and increase the reliability of the inspection process. A typical U.S. Pat. No. 4,066,363 granted Jan. 3, 1978, to J. W. Juvinall, and assigned to the assignee of the present invention, was designed to detect refractive defects and, more specifically, ribbon tear defects. A ribbon tear defect has at least a portion thereof defined by a pair of indentations running generally parallel along the outside surface of the sidewall of the container and a corresponding concavity between the indentations running along the inside surface of the sidewall of the container. The inspection device identifies ribbon tear defects by sensing light refracted by the concavity of the ribbon tear. However, the inspection device is incapable of detecting transverse ribbon tear defects, i.e., those defects running perpendicular to the longitudinal axis of the glass container because of the configuration of the optics associated with the device. Such inspection devices provide a signal to reject a glass container only upon the detection of a refractive defect having a longitudinal component. Therefore, a predominantly transverse defect would not be detected by existing inspection devices.

SUMMARY OF THE INVENTION

The present invention is directed to a method for detecting a transverse refractive defect in the sidewall of a transparent container. The method comprises the steps of directing a filtered source of diffused light toward the sidewall of the container to provide a longitudinal intensity gradient varying in a direction substantially parallel with the longitudinal axis of the container and sensing the intensity of light at a plurality of positions in a field-of-view aligned along a path in the plane of the sidewall and generally parallel with the longitudinal axis of the container. The method further comprises the step of producing a plurality of pixel signals each having a magnitude corresponding to the intensity of the light sensed at each position in the field-of-view. The shape of the wave train of intensity signals corresponds to the longitudinal intensity gradient in the absence of a transverse refractive defect and a detectable defect signature superimposed on the longitudinal gradient in the presence of a transverse refractive defect. The method also comprises the step of analyzing the wave train of intensity signals to detect the presence of a defect signature and to produce a defect signal in response thereto. In addition, the method comprises the step of rejecting the container in response to the defect signal that identifies a superimposed signature in the presence of a transverse refractive defect. Although existing inspection devices do not identify transverse refractive defects, this method enhances the sensed optical characteristics of a transverse defect using only a filter having a longitudinal gradient without using complex optics. The optical enhancement provides a signal to identify the superimposed signature which is then processed to provide a signal to reject the container in response to the identified signature. It is, therefore, an object of the invention to enhance and detect transverse refractive defects, and more specifically, transverse ribbon tears without complex optics. It is also an object of the invention to enhance and detect transverse refractive defects by a method compatible with methods for detecting longitudinal defects.

DETAILED DESCRIPTION OF THE INVENTION

Figures 1, 2, 3:
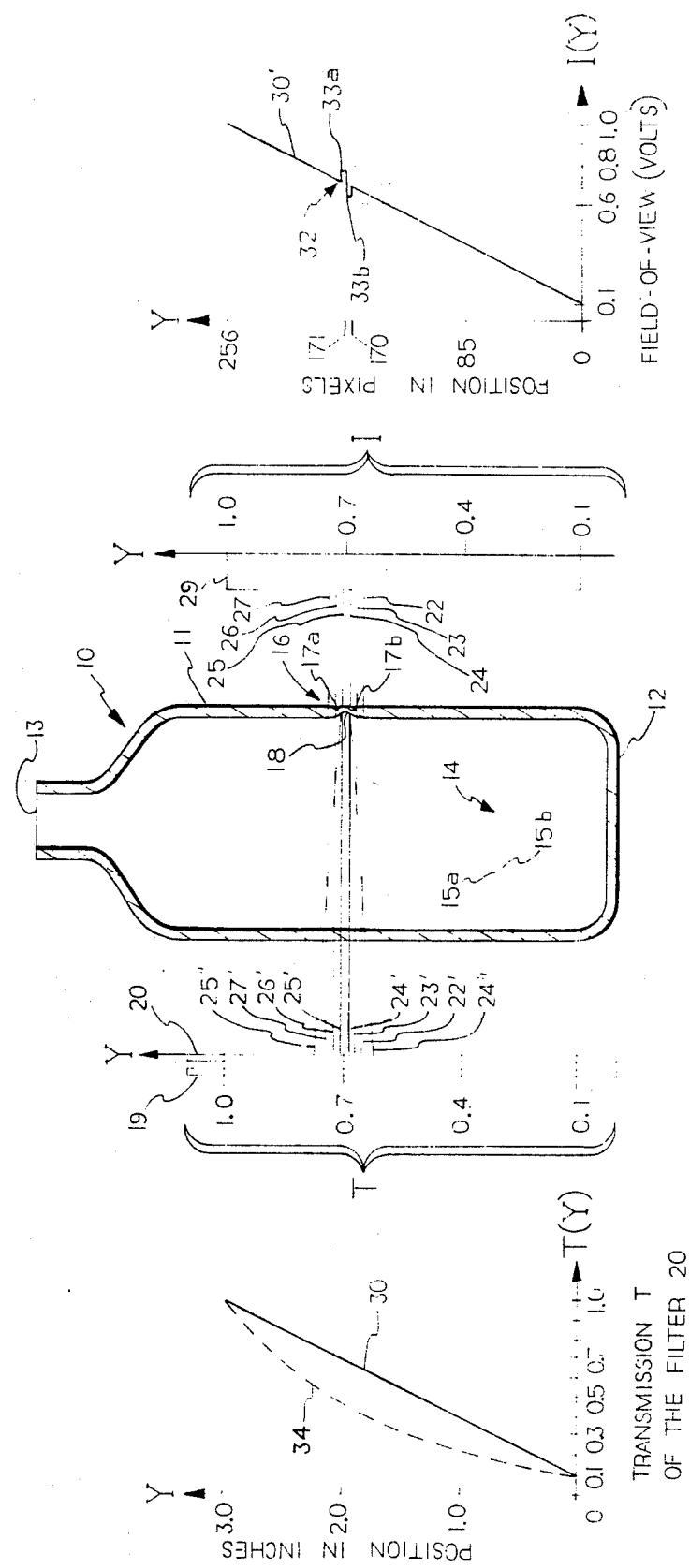
FIG. 1 is a partially schematic, vertical sectional view of a glass container and a filter and camera for detecting a transverse refractive defect in the glass container according to the invention.
FIG. 2 is a graph of the longitudinal transmission gradient of the filter of FIG. 1 in accordance with the invention.
FIG. 3 is a graph of the intensity gradient along the field-of-view of the sidewall as seen by the camera of FIG. 1 including the signature of a transverse refractive defect in accordance with the invention.

Referring in more detail to FIG. 1, the cross section of a transparent glass container is shown generally at 10 and comprises a tubular sidewall 11 terminating at the lower end in a bottom 12 and opening at the upper end to an annular rim 13. The container 10 is typically formed by forcing gas into the interior of a body of semimolten glass in a mold. While the glass body expands against the interior surfaces of the mold to form the container 10, various types of defects can also be formed, some of which require the container 10 to be rejected. These defects can be categorized, practically speaking, as refractive, reflective or absorptive defects. Although existing inspection devices are capable of detecting refractive defects, they are not capable of detecting transverse refractive defects, i.e., those defects running in a direction substantially perpendicular or transverse to the longitudinal axis of the container 10, because of the configuration of their optical sensors. The present invention is directed to a method for detecting a transverse refractive defect in the sidewall 11 of the container 10. A typical transverse refractive defect is a ribbon tear defect as indicated generally at 14 on the sidewall 11 of the container 10. The ribbon tear defect 14 has at least a portion thereof defined by a pair of indentations 15a and 15b running generally parallel along the outside surface of the sidewall 11 of the container 10 and a corresponding concavity between the indentations 15a and 15b running along the inside surface of the sidewall 11 of the container 10.

The cross section of another ribbon tear defect is illustrated generally at 16. The size of the defect 16 relative to that of the container 10 has been exaggerated to better illustrate its indentations 17a and 17b running along the outside surface of the sidewall 11 as well as its concavity 18 between the indentations 17a and 17b running along the inside surface of the sidewall 11. The transverse concavity 18 cannot be detected with the isotropic light sources used by existing inspecting devices. Rather, the instant invention directs a source 19 of diffused light toward the sidewall 11 of the container 10 and then filters the diffused light to provide a nonisotropic intensity distribution having a longitudinal gradient. A filter 20 having a longitudinal transmission gradient, i.e., the density of the filter varying in a direction parallel to the longitudinal axis of the container 10, is positioned adjacent the diffused source 19 to illuminate the sidewall 11. A solid-state camera 29 is positioned to view the filter 20 through the sidewall 11. The camera 29 comprises a linear array of 256 photosensitive devices (not shown), or pixels, aligned in a direction parallel with the longitudinal axis of the container 10 and a lens (not shown) which collimates the pixels to view a field aligned along a path in the plane of the sidewall 11 which is generally parallel with the longitudinal axis of the container 10. The collimation directs the line-of-sight of each pixel through a corresponding position in the field-of-view on the sidewall, as illustrated by the flux lines 22 to 27, to the filter 20 as illustrated by flux lines 22′ to 27′. Because of the collimation, the intensity sensed by the pixels at all positions in the field-of-view should correspond to the longitudinal gradient of the filter 20. The camera 29 can be, for example, type No. LC110 which have been available from EG & G Reticon located at Sunnyvale, Calif.

Figure 4:
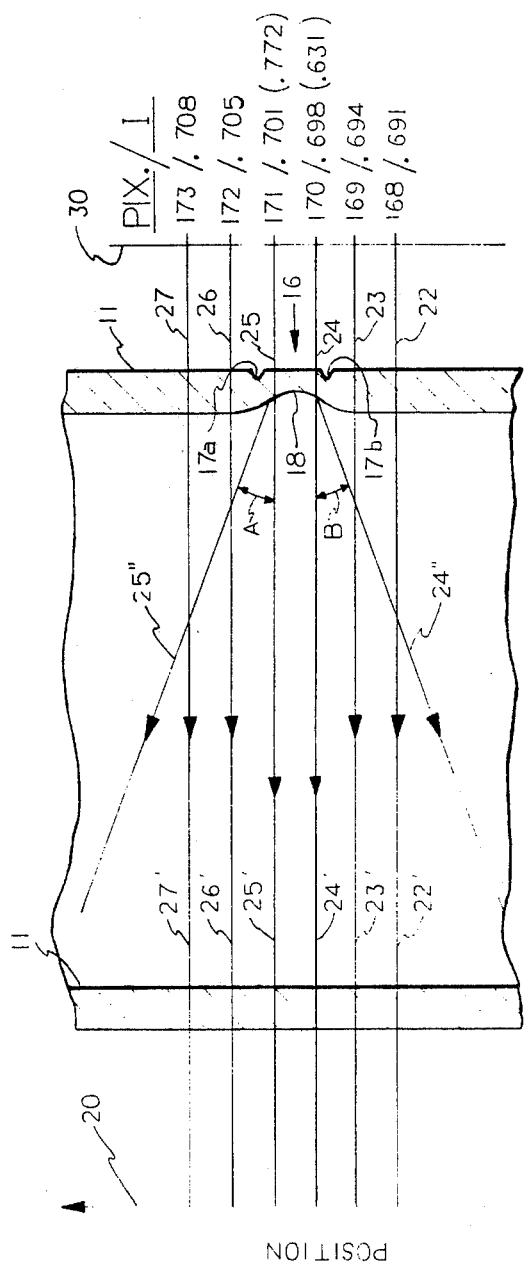
FIG. 4 is an enlarged fragmentary, vertical sectional view of the glass container and the filter and camera of FIG. 1.

Referring to FIG. 2, a graph of the transmission-characteristic curve of the filter 20 is illustrated at 30 and shows a plot of the normalized transmitted intensity T as a function of various positions along the height Y of the filter 20. The normalized transmitted intensity T is the ratio of the exitance to the incidence. Although the transmitted intensity T is a function of position Y along the filter 20, the graph 30 is oriented to better illustrate that the transmitted intensity T of the filter 20 varies longitudinally along the height Y from the top of the filter 20 to the bottom. The graph 30 shows that the longitudinal gradient varies linearly so that the transmitted intensity T varies from bright at the top of the filter 20, e.g., 100% transmission (T) at 3.0 inches (Y) through a gray region to dark at the bottom, e.g., 10% transmission (T) at zero inches (Y). As already described, the intensity sensed by the pixels at all points should correspond to the longitudinal gradient of the filter 20 absent a defect. The intensity I of the light at each position in the field-of-view is sensed by a corresponding one of the 256 pixels of the camera 29 which provides a plurality of pixel signals having a magnitude corresponding to the light sensed at each position. Referring more specifically to FIG. 4, a graph showing the magnitude of each pixel signal for each pixel of the camera 29 is illustrated at 30′. The magnitudes of the pixel signals fall within a voltage range, e.g., 0.1 volt to 1.0 volt, corresponding in value to the range of transmitted intensities T. As can be seen, the shape of the graph 30′, or wave train of pixel signals, representing the intensity I of the light at each position in the plane of the sidewall 11 corresponds to the longitudinal intensity gradient provided by the filter 20 absent a transverse refractive defect.

The presence of a transverse refractive defect in the sidewall 11 is optically enhanced by the longitudinal gradient provided by the filter 20. Commercial standards make it desirable to detect transverse refractive defects having a longitudinal component as small as 0.02 inch. Thus, the light must be sensed by the pixels at a sufficient number of positions per unit-length to obtain the necessary resolution to detect a defect having a longitudinal component as small as 0.02 inch. It has been found that the camera 29 must be collimated to view at least 85.0 positions per inch along the sidewall 11 of the container 10 to sufficiently enhance a 0.02 inch defect for detection. In other words, each pixel of the camera 29 senses the intensity I of light at a position in the field-of-view along the sidewall 11 having a height of approximately 0.01 inch. Therefore, given the availability of 256 pixels in the camera, three inches of the field comprising 256 segments can be viewed. Referring to FIG. 4, the sidewall 11 and the defect 16 are shown enlarged to better illustrate how the concavity 18 affects the collimated line-of-sight of the pixels. When a transverse refractive defect, such as the ribbon tear defect 16, in the sidewall 11 has a longitudinal component larger than 0.02 inch, the concavity 18 of the defect 16 behaves optically like the concave surface of a planoconcave lens. For example, the view of pixel #171 along the flux line 25 is directed to a position in the field-of-view adjacent the upper portion of the concavity 18. As a result, the view of pixel #171 is refracted by the upper portion of the concavity 18 to a brighter point of higher transmission on the filter 20 as indicated by a diverging flux line 25″. Correspondingly, the view of pixel #170 along the flux line 24 is directed to a position in the field-of-view adjacent the lower portion of the concavity 18 and is refracted to a darker point of lower transmission on the filter 20 as indicated by a diverging flux line 24.″ Because of these refractions, a bright spot appears adjacent a dark spot on a relatively gray background in the field-of-view of the camera 29. As illustrated in FIG. 3, the parallel bright and dark spots represent an optically enhanced ribbon tear defect 16 sensed by the pixels #171 and #170, respectively, of the camera 29 which produces a ribbon tear signature 32 having a positive component 33a of greater intensity and a negative component 33b of lesser intensity with respect to the relatively constant DC signal produced by the wave train 30′ of intensities corresponding to the longitudinal gradient of the filter 20.

Figure 5:
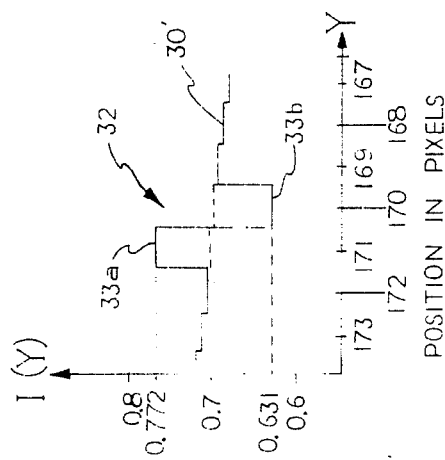
FIG. 5 is an enlarged fragmentary view of the signature of a transverse defect in the graph of FIG. 4 turned through an angle of 90.

Referring to FIG. 5, an enlarged fragmentary view of the ribbon tear signature 32 superimposed on the wave train 30′ of pixel pulses of FIG. 3 is shown. FIGS. 3, 4 and 5 will now be referred to in more detail through a specific example. Using FIG. 5, the enlarged version of FIG. 4, the voltage representing the intensity I sensed by each pixel is provided by the camera 29 as shown in FIG. 3 and in Table I below. Absent a defect, the intensity of the wave train 30′ corresponds to the longitudinal gradient 30 of the filter 20 and lineally steps to produce an essentially DC signal as indicated by the steps of small magnitude in FIG. 5.

TABLE I

| PIXEL | FLUX LINE | INTENSITY |
|---|---|---|
| 173 | 27 | 0.708 |
| 172 | 26 | 0.705 |
| 171 | 25 | 0.701 |
| 170 | 24 | 0.698 |
| 169 | 23 | 0.694 |
| 168 | 22 | 0.691 |

TABLE II

| FLUX LINE | INTENSITY |
|---|---|
| 25" | 0.772 |
| 24" | 0.631 |

However, in the presence of the ribbon tear defect 16, which behaves optically like a plano-concave lens, the view of pixel #171 of the camera 29 is refracted A° by the upper portion of the concavity 18. Thus, the pixel #171 senses a brighter intensity I of 0.772 volt (Table II) from a point higher on the filter 20 as indicated by the flux line 25", rather than the grayer intensity I of 0.701 volt that would be sensed in the absence of the upper portion of the concavity 18 from an opposing point on the filter 20 as indicated by the flux line 25'. Consequently, the pixel #171 of the camera 29 sees the bright enhancement, the bright spot referred to above, which produces the positive portion 33a of the ribbon tear signature 32. Correspondingly, the view of pixel #170 the camera 29 is refracted B° by the lower portion of the concavity 18. Thus, pixel #170 senses a darker intensity I of 0.631 volt (Table II) from a point lower on the filter 20 as indicated by the flux line 24", rather than the brighter intensity I of 0.698 volt that would be sensed in the absence of the lower portion of the concavity 18 from an opposing point on the filter 20 as indicated by the flux line 24'. Consequently, pixel #170 of the camera 29 sees the dark enhancement, the dark spot referred to above, and produces the negative portion 33b of the ribbon tear signature 32. Furthermore, the bright in dark enhancement appear on a relatively gray background in the field-of-view of the camera 29 because an intermediate intensity I of approximately 0.7 volt is sensed at positions on either side as indicated by flux lines 22', 23', 26', and 27'.

Figure 6:
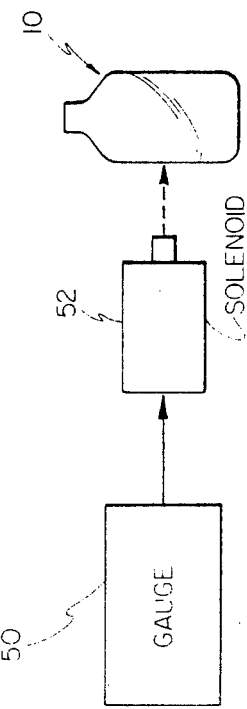
FIG. 6 is a schematic drawing of a container rejection station.

The pixel signals are then provided to a gauge 50 (FIG. 6) such as, for example, Model RBI which has been available from Inex Corporation located at Denver, Colo. The gauge includes a device which stores the pixel signals and analyzes the signals by calculating the difference between the magnitudes of adjacent pixel signals for successive pairs of pixels. In a system that computes the difference between pixel signals, the preferred embodiment requires that the filter 20 have a longitudinal transmission gradient that is linear, as the one used in the example above, to make the data longitudinally space invariant, i.e., the signature of a defect is the same regardless of the longitudinal location of the defect on the container. Thus, the signature of a defect will produce the same difference-voltage level regardless of its location on the wave train of pixel signals. When the absolute value of a pixel difference signal exceeds a predetermined value to detect a signature, such as the positive 33a or negative 33b portion of the ribbon tear signature 32, the gauge provides a defect signal to a solenoid 52 for rejecting the defective container 10 in response to the detected signature.

The pixel signals can also be provided to a gauge such as, for example, the type disclosed in U.S. patent application Ser. No. 205,054, filed Nov. 7, 1980, in the name of John W. V. Miller and entitled "METHOD AND APPARATUS FOR RAPIDLY EXTRACTING SIGNIFICANT DATA FROM A SPARSE OBJECT", assigned to the assignee of the present invention and incorporated herein by reference. This gauge analyzes the signals by calculating the ratio between the magnitudes of adjacent pixel signals for successive pairs of pixels. In a system that computes the ratio between pixel signals, the preferred embodiment requires that the filter 20 have a longitudinal transmission gradient that is logarithmic to make the data longitudinally space invariant. For example, for a filter having a transmission gradient varying from 0.1 to 1.0 in three inches, there would be an approximately 47% increase in transmission per half inch ($\sqrt[6]{1.0/0.1} = 1.47$) as shown in Table III below and as illustrated by a dashed line 34 in FIG. 2. As a result, the ratio

TABLE III

| Position in inches on filter (Y) | Transmission (T) of filter |
|---|---|
| 3.0 | 1.00 |
| 2.5 | 0.68 |
| 2.0 | 0.46 |
| 1.5 | 0.32 |
| 1.0 | 0.22 |
| 0.5 | 0.15 |
| 0.0 | 0.10 | between adjacent pixels, absent a defect, is uniform from the top of the filter to the bottom. Also, the signature of a defect will produce the same ratio-voltage level regardless of its location on the wave train of pixel signals. When the pixel ratio signal varies by more than a predetermined value from the corresponding logrithmic ratio fixed by the filter between adjacent positions to detect signature, the computer provides a defect signal to a station for rejecting the defective container 10 in response to the detected signature.

The filter of the instant invention, whether its longitudinal gradient is linear or logarithmic, is especially useful because its use is compatible with filters having a spectrum with a transverse gradient, i.e., a transmission gradient varying in a direction perpendicular to the longitudinal axis of the container 10 and parallel to the flow of containers along a conveyor. A filter having a transverse gradient is sometimes used to detect vertical refractive defects and distinguish them from absorption defects.

The foregoing disclosure is the best mode devised by the inventor for practicing this invention. It is apparent, however, to one skilled in the pertinent art that various changes may be made in details of construction from those shown in the attached drawings and discussed in conjunction therewith without departing from the spirit and scope of this invention. The detail in the foregoing disclosure is intended to enable one skilled in the pertinent art to practice the instant invention. Therefore, it is to be understood that this invention is not to be limited to the specific details shown and described.

What I claim is:

1. A method for detecting a refractive defect in the sidewall of a transparent container, the defect being oriented in a direction substantively transverse to the longitudinal axis of the container, comprising the steps of:

directing a filtered source of diffused light toward the sidewall of the container to provide an intensity gradient which varies in a predetermined direction relative to the longitudinal axis of the container;

sensing the intensity of light at a plurality of positions in a field-of-view aligned along a path generally parallel to said predetermined direction;

producing a plurality of pixel signals each having a magnitude corresponding to the intensity of the light sensed at each position in the field-of-view, whereby the shape of the wave train of pixel signals corresponds to said intensity gradient in the absence of a refractive defect and a detectable defect signature superimposed on said intensity gradient in the presence of a refractive defect;

analyzing the wave train of pixel signals to detect the presence of a defect signature; and rejecting the container in response to a defect signal provided in response to a detected defect signature, whereby the defective container is sorted out from otherwise commercially acceptable containers.

2. The method set forth in claim 1 for detecting defects transverse to the longitudinal axis of the container wherein said intensity gradient varies as a function of direction substantially parallel to the longitudinal axis of the container.

3. A method as recited in claim 2 wherein the longitudinal intensity gradient is linear and wherein the step for analyzing the wave train of pixel signals is accomplished by calculating successive differences between adjacent pixel signals to provide difference signals so that a defect signature is detected when any one of the difference signals exceeds a predetermined value.

4. A method as recited in claim 2 wherein the longitudinal intensity gradient is logarithmic and wherein the step for analyzing the train of pixel signals is accomplished by calculating successive ratios between adjacent pixel signals to provide ratio signals so that a defect signature is detected when any one of the ratio signals varies by more than a predetermined value from the corresponding logarithmic ratio fixed by the filter.

5. A method as recited in claims 2, 3, or 4 wherein light at a sufficient number of positions per unit-length along the generally longitudinal path is sensed to detect a transverse refractive defect having a narrow longitudinal component.

6. A method as recited in claim 5 wherein the intensity of light at a minimum of at least 85.0 positions per inch is sensed to detect a transverse refractive defect having a narrow longitudinal component as small as 0.02 inch.

* * * * *

UNITED STATES PATENT AND TRADEMARK OFFICE
CERTIFICATE OF CORRECTION

PATENT NO. : 4,487,322

DATED : December 11, 1984

INVENTOR(S) : John W. Juvinall

It is certified that error appears in the above-identified patent and that said Letters Patent are hereby corrected as shown below:

Col. 1, line 24, after typical insert --inspection device, such as, for example, that disclosed in--

Signed and Sealed this

Thirtieth Day of April 1985

[SEAL]

Attest:

DONALD J. QUIGG

Attesting Officer

Acting Commissioner of Patents and Trademarks